(12) United States Patent
Lee et al.

(10) Patent No.: US 6,997,040 B1
(45) Date of Patent: Feb. 14, 2006

(54) GAS SENSOR AND FABRICATION METHOD THEREOF

(75) Inventors: Won-Bae Lee, Taejeon (KR); Ho-Jun Lee, Taejeon (KR)

(73) Assignee: Seju Engineering Co., Ltd., Daejon (KR)

( * ) Notice: Subject to any disclaimer, the term of this patent is extended or adjusted under 35 U.S.C. 154(b) by 193 days.

(21) Appl. No.: 10/110,209

(22) PCT Filed: Oct. 17, 2000

(86) PCT No.: PCT/KR00/01161

§ 371 (c)(1),
(2), (4) Date: Apr. 18, 2002

(87) PCT Pub. No.: WO01/28915

PCT Pub. Date: Apr. 26, 2001

(30) Foreign Application Priority Data

Oct. 19, 1999 (KR) .............................. 1999/45306

(51) Int. Cl.
*G01N 7/00* (2006.01)
(52) U.S. Cl. ...................... 73/31.05; 73/23.2
(58) Field of Classification Search ............. 73/31.05, 73/29.2, 31.06, 23.2; 422/98
See application file for complete search history.

(56) References Cited

U.S. PATENT DOCUMENTS

| | | | |
|---|---|---|---|
| 4,580,439 A * | 4/1986 | Manaka ...................... 73/31.06 |
| 4,720,394 A | 1/1988 | Kojima et al. |
| 4,953,387 A * | 9/1990 | Johnson et al. ............. 73/25.03 |
| 4,984,446 A * | 1/1991 | Yagawara et al. .......... 73/31.06 |
| 5,401,376 A | 3/1995 | Foos et al. |
| 5,565,084 A | 10/1996 | Lee et al. .................... 205/646 |
| 5,759,367 A | 6/1998 | Matsuura et al. |
| 5,763,782 A * | 6/1998 | Moore et al. ............. 73/514.18 |
| 5,783,154 A * | 7/1998 | Althainz et al. .............. 422/98 |
| 5,902,556 A * | 5/1999 | Van De Vyver et al. .... 422/174 |

FOREIGN PATENT DOCUMENTS

| | | |
|---|---|---|
| EP | 0751389 | 1/1997 |
| JP | 63259459 | 10/1988 |
| JP | 1-313751 | 12/1989 |
| JP | 6-347432 | 12/1994 |
| JP | 11166942 | 6/1999 |

OTHER PUBLICATIONS

English Language Abstract of JP 1-313751.
English Language Abstract of JP 11-166942.
English Language Abstract of JP 6-347432.

* cited by examiner

*Primary Examiner*—Hezron Williams
*Assistant Examiner*—Rodney Frank
(74) *Attorney, Agent, or Firm*—Greenblum & Bernstein, P.L.C.

(57) ABSTRACT

A gas sensor includes a silicon substrate provided with a recess, an insulating layer, a first and a second conductive patterned layers and a detecting portion for sensing a gas which passes there through. In the gas sensor, the insulating layer is formed on a top portion of the silicon substrate which does not form the recess. The first and the second conductive patterned layers extend over the recess, thereby being apart from the silicon substrate physically. The detecting portion is formed on both portions of the first and the second conductive patterned layers.

11 Claims, 8 Drawing Sheets

GAS SENSOR AND FABRICATION METHOD THEREOF

TECHNICAL FIELD

The present invention relates to a gas sensor and fabrication method thereof; and, more particularly, to the gas sensor with an enhanced sensitivity, low power consumption, a low heat capacity and heat loss, and fabrication method thereof, wherein a heating line and a sensing line are formed being apart from a substrate by using a semiconductor manufacturing process and a ceramic bulk of gas sensitive material are formed extending over the heat and the sensing lines.

BACKGROUND ART

Generally, a ceramic gas sensor is to detect particular gas. When the gas sensor is exposed on particular gas, a conductivity of ceramic as gas sensitive material is changed or an electromotive force thereof is generated so that it is possible to detect particular gas by measuring the conductivity or the electromotive force. In the ceramic gas sensor as above, to improve sensitivity and selectivity for particular gas, catalytic material is doped into the ceramic and further, the temperature should be kept higher than 300° C. Hence, power consumption of the ceramic gas sensor is higher than that of the other ones. Therefore, in order to enlarge the application range of the ceramic gas sensor, it is most important to provide the ceramic gas sensor with low power consumption but keeping the ceramic at high temperature.

Referring to FIG. 1, there is provided a cross sectional view of a conventional gas sensor 100 disclosed in U.S. Pat. No. 5,759,367 titled "GAS SENSOR". The conventional gas sensor comprises an insulating glass film 4 formed on a silicon substrate, heater films 8, 10, made of gold (Au), which are formed on top of the insulating glass film 4, an insulating layer 14, detection electrodes 18, 20, formed on top of the insulating layer 14, and a gas sensitive film 16 surrounding the detection electrodes 18, 20. In this gas sensor 100, the heater film 6 heats up the gas sensitive film 16 and a variation of the gas sensitive film 16 is detected according to the change of the gas flown thereinto, by using the detection electrodes 18, 20.

The gas sensor 100 as aforementioned has a drawback that the gas sensitive film 16 is disposed on the detection electrodes 18, 20 so that the fabrication process becomes complicated. That is, each mask is needed for patterning the heater films 8, 10 and the detection electrodes 18, 20, respectively. Moreover, since the gas sensitive film 16 is formed on a top surface of the heater film 6 and a bottom portion of the heater film 6 is directly in contact with the insulating glass film 4, the heat loss into the silicon substrate becomes considerably raised.

DISCLOSURE OF INVENTION

It is, therefore, an object of the present invention to provide a gas sensor with characteristics of an enhanced sensitivity, a minimized heat capacity and loss, wherein a heating line and a sensing line are apart from a silicon substrate and a ceramic of a gas sensitive material is formed in a bulky shape extending over the heat and the sensing lines.

It is, therefore, another object of the present invention to provide a method for fabricating the gas sensor with characteristics of an enhanced sensitivity, a minimized heat capacity and loss.

In accordance with an embodiment of the present invention, there is provided a gas sensor, comprising: a silicon substrate provided with a recess formed by patterning into a predetermined depth; an insulating layer formed on top of the silicon substrate except the recess; a first conductive patterned layer crossing the recess and being fixed to the insulating layer, to electrically be isolated from the silicon substrate; a second conductive patterned layer patterned layer crossing the recess and being fixed to the insulating layer, to electrically be isolated from the silicon substrate and the first conductive patterned layer; and a gas detecting portion formed on both predetermined portions of the first and the second conductive patterned layers.

In accordance with another embodiment of the present invention, there is provided a method for manufacturing a gas sensor, the method comprising the steps of: a) forming an insulating layer on a silicon substrate; b) forming a window by patterning a portion of the insulating layer; c) forming a first and a second metal patterns upon the silicon substrate exposed by the window and the insulating layer; d) separating the first and the second metal patterns from the silicon substrate by dipping the silicon substrate into alkaline aqueous solution to pattern the substrate exposed to the window and to form a recess with a shape of the window; and e) forming a gas detecting portion on both predetermined portions of the first and the second metal patterns which are formed over the recess.

BRIEF DESCRIPTION OF THE DRAWINGS

Other objects and aspects of the invention will become apparent from the following description of the embodiments with reference to the accompanying drawings, in which.

BEST MODE FOR CARRYING OUT THE INVENTION

Hereinafter, preferred embodiments of the present invention will now be described in detail, with reference to the accompanying drawings.

Figure 1:
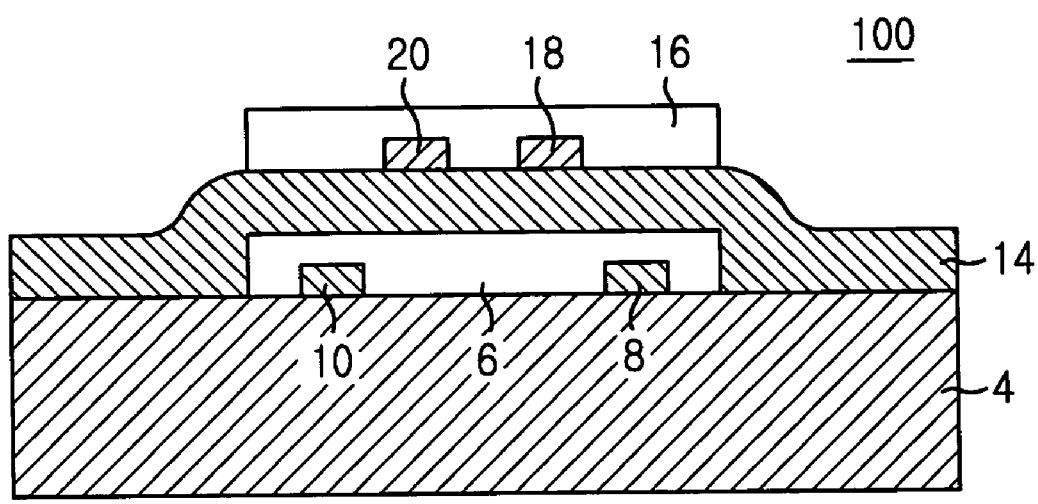
FIG. 1 is a cross sectional view of a conventional gas sensor.
Figure 2:
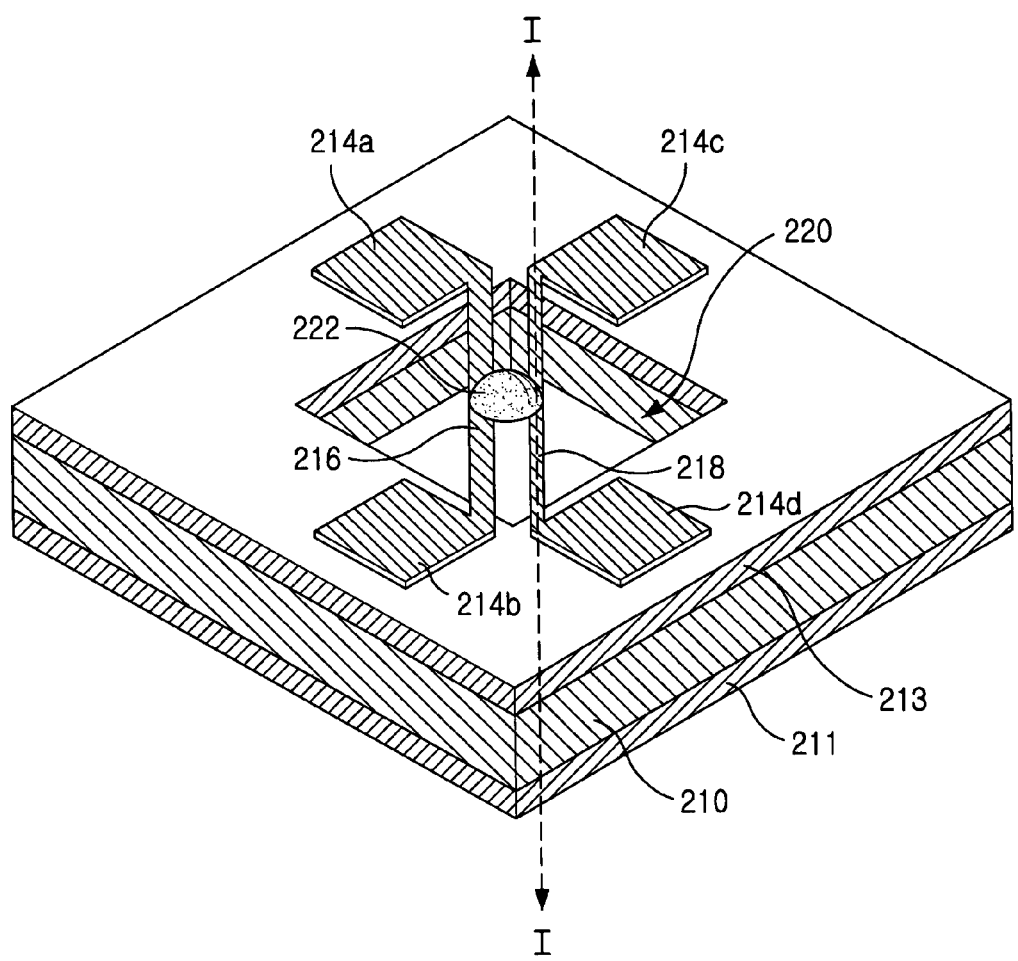
FIG. 2 is a perspective view of a gas sensor in accordance with the present invention.

Referring to FIG. 2, there is shown a perspective view of a gas sensor 200 of the present invention. In this figure, an insulating layer 212 is formed on top of a silicon substrate 210. For example, the insulating layer 212 is made of material such as silicon oxide, silicon nitride, silicon carbide or the like. The insulating layer 212 is formed with a thickness ranging from approximately 0.1 to approximately 10 $\mu$m, preferably of 2 $\mu$m. Furthermore, it is preferable that the silicon substrate has a crystal orientation of <100>.

In a center of the silicon substrate 210, there is a recess 220 formed after stripping off the insulating layer 212. The recess 220 has a rectangular shape with a predetermined depth. For the sake of a fabrication facility, it is preferable that the recess is formed in a shape of the rectangular but it can be formed in the shape of a circle or the other types. Over this rectangular recess, there are the heating line 216 and the sensing line 218 running parallel with each other.

This heating line 216 and sensing line 218 are extended over the rectangular recess 220 being apart from the substrate 210.

As shown in FIG. 2, the heating line 216 and the sensing line 218 are connected to metal pads 214A, 214B, 214C and 214D respectively which are formed on top of the insulating layer 212. The metal pads 214A, 214B, 214C and 214D are formed on the insulating layer 212 to electrically be isolated from the silicon substrate 210 and to electrically be connected to an outer power or an outer circuit. Here, it is preferable that a metal pattern including the metal pads 214A, 214B, 214C and 214D, the heating line 216 and the sensing line 218, are formed in a unit body. That is, the metal pads 214A, 214B and the heating line 216 are formed in a unit body, while the sensing line 218 and the other metal pads 214C, 214D are formed in a unit body.

The metal pattern such as above is preferably made of material such as platinum (Pt), nickel (Ni) coated with gold (Au) or palladium (Pd), and poly-crystal silicon film doped with boron (B). Preferably, the thickness of the metal pattern is approximately 0.1 to approximately 20 $\mu$m, most preferably of 5 $\mu$m. Furthermore, a ceramic bulk 222 is placed upon both of the heating line 216 and the sensing line 218 running parallel with each other. Here, the ceramic bulk 222 has gas sensitive material made of a combustible material such as ethanol, methane, LPG or the like, and a semiconductor material such as $SnO_2$, ZnO, $Fe_2O_3$ or the like, for detecting carbon oxide (CaO). And to improve the sensitivity of gas sensitive material, it is possible to be doped with a catalytic material such as Pt, Pd, with concentration of 0.5~1 wt. %.

An operation mechanism of the ceramic gas sensor is illustrated as followings. When an electrical current is supplied to the heating line 216, heat is produced due to a resistance of the heating line 216 and temperature of the ceramic bulk 222 increases also. At this time, air including the gas for detection is flown into the ceramic bulk 222 so that a resistivity of the ceramic bulk 222 is changed, wherein the resistivity of the ceramic bulk 222 is measured by measuring a resistance between the heating line 216 and the sensing line 218.

A method of measuring the resistivity of the ceramic bulk 222, for example, is illustrated hereinafter. To begin with, both ends of the heating line 216 is connected to a heater power, and then a circuit is prepared such a manner that one end of the sensing line 218 is connected to outer resistance ($R_1$) of the substrate and voltage ($V_{cc}$) is supplied to an end of the outer resistance ($R_1$). At this time, as illustrated already, heater voltage ($V_H$) is supplied by the heater power so that heat produced by the resistance of the heating line 216 makes temperature of the ceramic bulk 222 raised up to detection temperature. At this temperature, voltage ($V_{cc}$) is measured at the end of the outer resistance so that it is possible to evaluate the resistance ($R_s$) of the ceramic bulk 222. Generally, assuming that the heater resistance ($R_H$) is several or tens of ohms ($\Omega$), the resistance of the ceramic bulk 222 is over than tens of K$\Omega$, and $V_H$ is sufficiently lower than $V_{cc}$, $V_{out}$ is calculated by a following equation so that the resistance ($R_s$) of the ceramic bulk 222 is evaluated.

$$V_{out} \approx [R_s/(R_1+R_s)] \times V_{cc}$$

It is noted that the equation above can be used to evaluate the value approximately under the above assumptions, but the more precise value will be calculated by using a more complicated equation in which there is not any assumption like above.

Therefore, since a change of the resistivity of the ceramic bulk 222 is related to a concentration of the particular gas included in air, it is possible to calculate the concentration of the particular gas in air from the measured resistance.

Next, referring to FIGS. 3A to 3E, there are provided cross sectional views setting forth a method for manufacturing the gas sensor of the present invention.

Figure 3A:
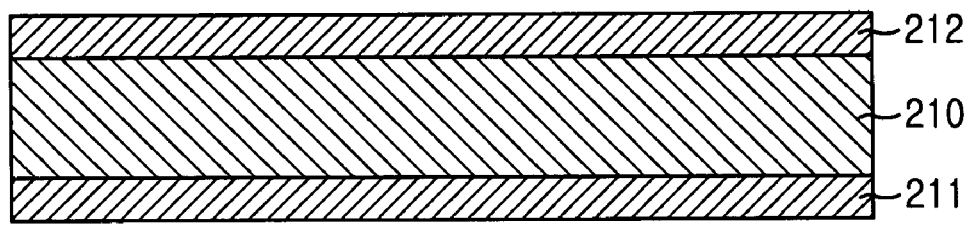
FIGS. 3A to 3E are cross-sectional views setting forth a method for manufacturing the gas sensor of the present invention, taken along the line I—I in FIG. 1.

Referring to FIG. 3A, insulating layers 211, 212 of which the thickness is wholly 0.1~10 $\mu$m, preferably 2 $\mu$m, are formed on both sides of the silicon substrate 210 with a crystal orientation of <100>. Here, the insulating layers 211, 212 are made of material such as silicon oxide, silicon nitride, silicon carbide or the like.

Figure 3B:
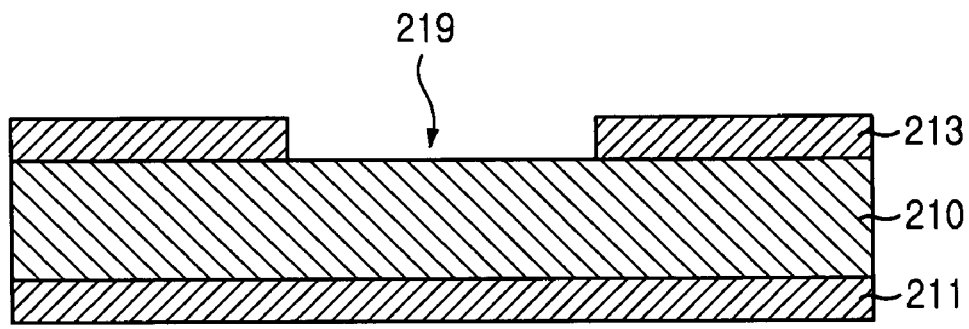

In ensuing step, referring to FIG. 3B, a center portion of one insulating layer 212 formed on one side of the silicon substrate 210 is patterned locally to obtain a window 219 and a patterned insulating layer 213. At this time, a portion of the silicon substrate 210 becomes exposed trough the window 219. The insulating layer 212 is patterned by using a conventional method such as a photolithography and an etching process used in semiconductor manufacturing process.

Figure 3C:
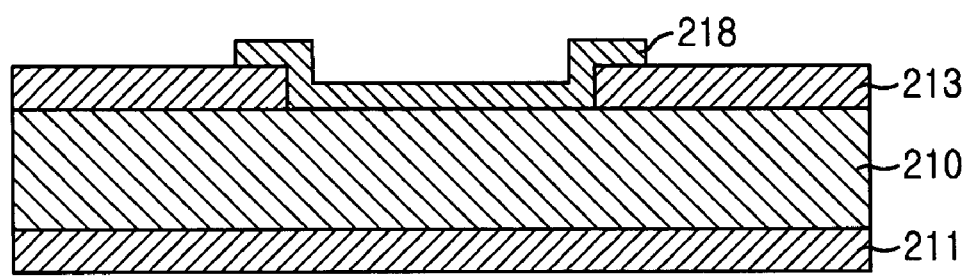

Thereafter, referring to FIG. 3C, a metal pattern is formed upon the window 219 and the patterned insulating layer 213, wherein the metal pattern includes a heater line 216 and a sensing line 218 formed on top of the window 219, metal pads 214A, 214B, 214C, 214D formed on top of the insulating layer 213. Here, the heating line 216 as described already, is formed as a resistance line in order to supply heat to the ceramic bulk 222, and the sensing line 218 is formed in order to measure the change of the resistance of the ceramic bulk 222. And the metal pads 214A, 214B, 214C, 214D are formed on top of the patterned insulating layer 213 for electrically being isolated from the silicon substrate 210. Furthermore, the metal pads 214A, 214B, 214C, 214D does not only support the heating line and sensing line but also provide a means for being connected to an output power or the other outer circuit. It is preferable that the metal pattern such as above is manufactured in a unit body of the metal pads 214A, 214B and the heating line 216, and in a unit body of the other metal pads 214C, 214D and the sensing line 218 in view of the fabrication facility. The thickness is preferably 0.1~20 $\mu$m, most preferably 5 $\mu$m. The metal pattern is preferably made of material such as platinum (Pt), nickel (Ni) doped with gold (Au) or palladium (Pd), and multi-crystal silicon film doped with boron (Br). In addition with that, to improve an adhesion between the metal pattern and the patterned insulating layer 213, it is possible to use Pt attached with Cr, wherein the thickness of Cr is preferably about 0.02 $\mu$m.

Figure 3D:
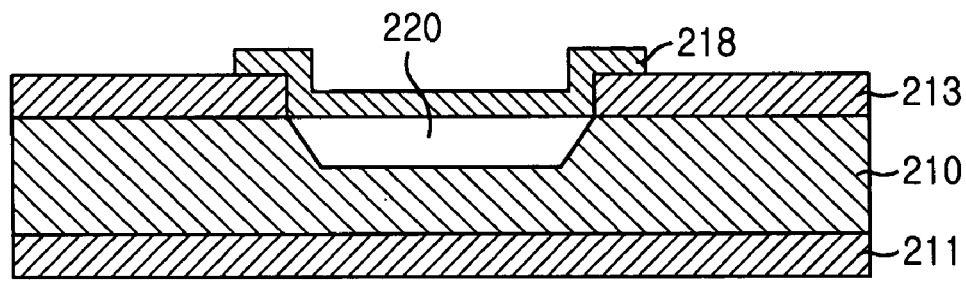

In a next step, referring to FIG. 3D, whole the silicon substrate 210 is dipped in alkaline aqueous solution, and the portion of the silicon substrate which exposed through the window 219 is patterned to a predetermined depth. Here, the insulating layer such as silicon oxide layer and the metal pattern such as Pt are not etched in alkaline aqueous solution so that a recess with the predetermined depth is formed on the silicon substrate 210. Thus, the heating line 216 and the sensing line 218 as shown in FIG. 2 and FIG. 3D, are apart from the silicon substrate by the recess 220. The alkaline aqueous solution used here, is potassium hydroxide or a mixture solution of ethylenediamine and pyrocatechol. For example, when the substrate is dipped in potassium hydroxide aqueous solution at 80° C. for 2 hours, the recess with the thickness of approximately 150 $\mu$m can be obtained.

Figure 3E:
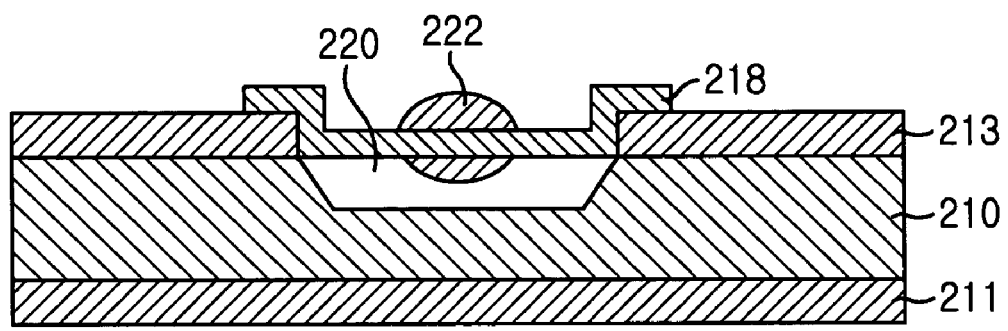

In ensuing step, referring to FIG. 3E, the ceramic bulk 222 is formed by thermal treatment after ceramic precursor droplet having a paste-shape is dropped over a predetermined range of the heating line 216 and the sensing line 218. Here, the ceramic precursor, for example, is made of a mixture having a composition of 90 weight % of $SnO_2$ as gas sensitive material, 9 weight % of silica sol as a binder, and 1 weight % of $PdCl_2$ as a catalyst. Upon the ceramic precursor having the composition above, α-tepineol including 5% of ethylcellulose is added with a predetermined amount, and then viscosity becomes hundreds of cps. Following this, the precursor is dropped over the heating line 216 and the sensing line 218 after making the precursor in paste-shape. The condition for the thermal treatment carried out after dropping the ceramic precursor droplet, is not limited if solvent included in the ceramic paste can be volatized.

As aforementioned, the gas sensor of the present invention is made by using a method such as a micro-machining technique based on a semiconductor fabrication method except the formation of the ceramic bulk. Thus, volumes of the heating line 216, the sensing line 218 and the ceramic bulk 222 are extremely small for use in the gas sensor 200 of the present invention. Further, the heating line 216, the sensing line 218 and the ceramic bulk 222 are apart form the silicon substrate so that the heat capacity and the loss are small. Moreover, because of using the ceramic bulk as a gas sensitive material in the gas sensor 200 of the present invention, the detection and the physical properties are superior to those of the other gas sensors which are utilized a thin film ceramic. In addition with that, the method of the present invention has an advantage that only two masks are needed for patterning the window 219 and the metal pattern. And further, mass productivity of batch process type which is a merit of semiconductor fabrication method is still applied to the manufacture of the gas sensor 200 of the present invention so that manufacturing cost can be lowered.

Meanwhile, referring to FIGS. 4A to 4F, there is provided a detecting portion including the heating line 216, the sensing line 218 and the ceramic bulk 222 in accordance with another embodiment of the present invention. As shown in FIG. 2, if the heating line and the sensing line are formed running parallel with each other and the ceramic bulk 222 is formed thereon, a portion of heat is only used for heating up the ceramic bulk 222 and the temperature of the ceramic bulk 222 becomes not uniform because the resistance is distributed uniformly over the heating line 216. This problem can be overcame by modifying the structure of the detecting portion as described in FIGS. 4A to 4F.

Figure 4A:
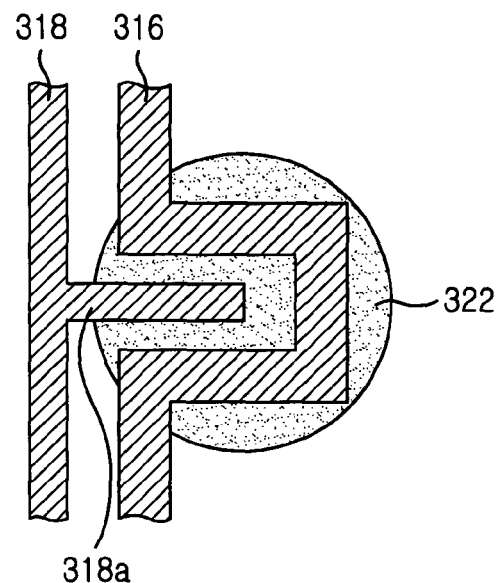
FIGS. 4A to 4F are cross sectional views of a detecting portion of the gas sensor in accordance with embodiments of the present invention.
Figure 4B:
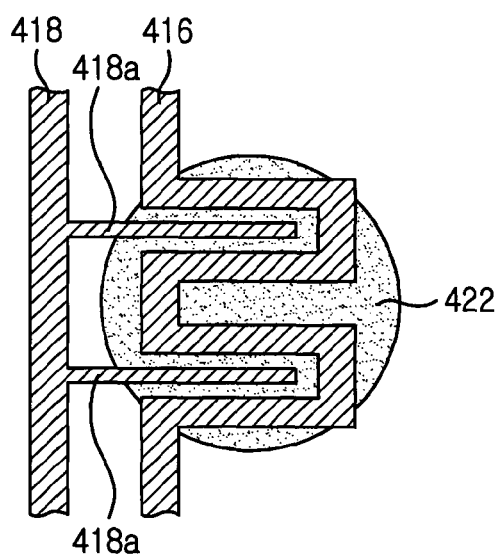
Figure 4C:
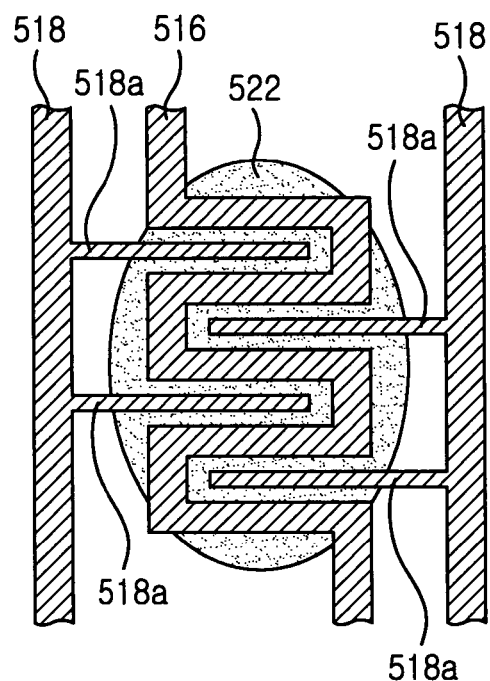

Referring to FIG. 4A, the heating line 316 is bended like "U", and a branch line 318A of the sensing line 318 is inserted a concave shape thereof. According to this structure, the resistance concentrates on the ceramic bulk 322 and further, heat spreads over the range of the ceramic bulk 322 so that the problem can be avoided and the detection property can be enhanced and the heat loss can decrease. Moreover, to improve the resistance concentration and uniform distribution of heat upon the ceramic bulk 322, the heating line 416 may be formed in a bended shape of zigzag as shown in FIG. 4B and the branch line 418A of the sensing line 418 may be inserted into concave shapes thereof from one direction. Further, the heating line 516 may be formed in a bended shape of zigzag and branch lines of two sensing lines 518 may be inserted into concave shapes thereof from both directions.

Figure 4D:
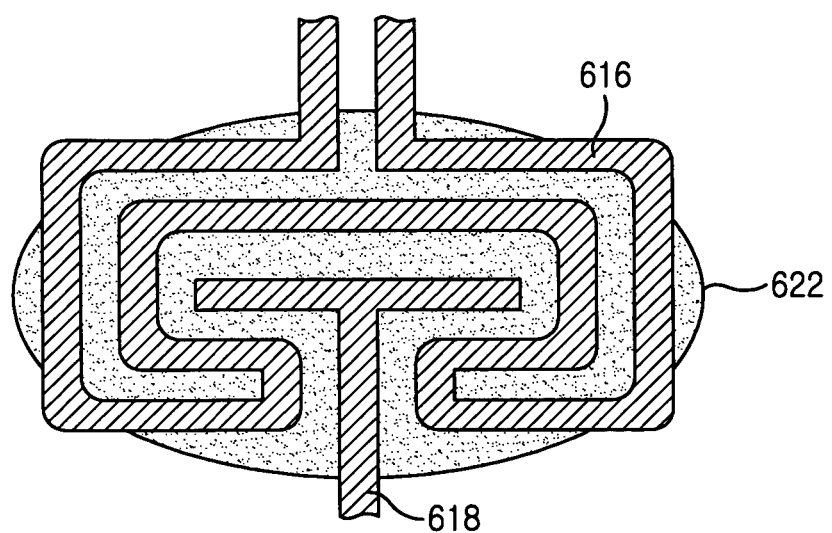
Figure 4E:
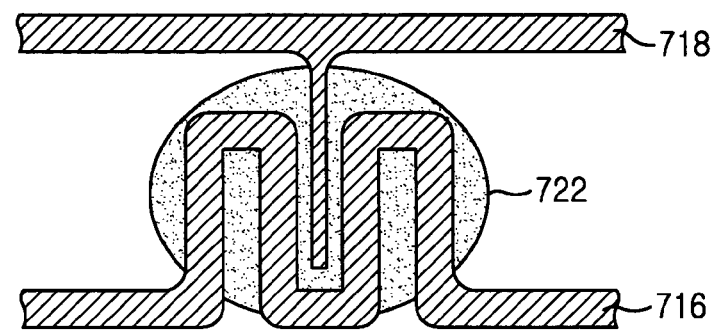
Figure 4F:
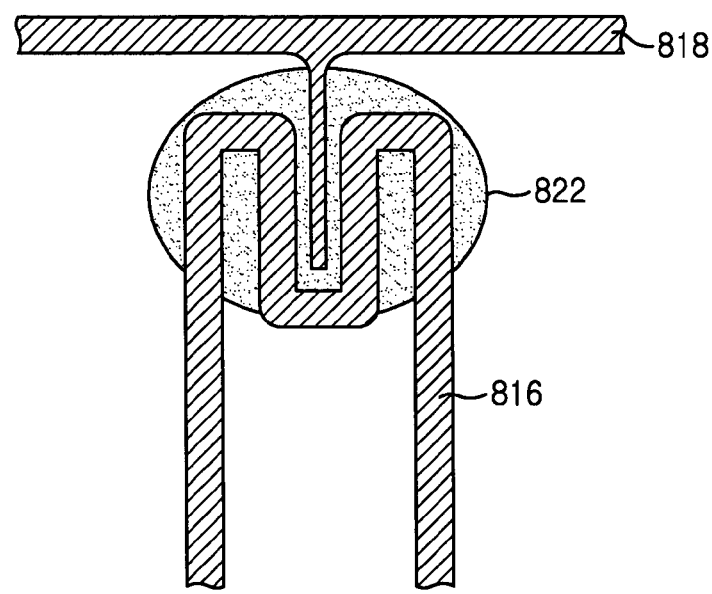

As shown in FIGS. 4D to 4F, since the change of the resistivity of the ceramic bulks 622, 722, 822 are depended on uniformly heating the ceramic bulk, the thickness of the heating lines 616, 716, 816 in the ceramic bulks 622, 722, 822 are designed to be more thicker than those of the sensing lines 618, 718, 818. Therefore, in accordance with the embodiment of the present invention, it is preferable that the width and the thickness of the sensing lines 618, 718, 818 are approximately 10 μm and 5 μm, respectively. Further, if the width and the thickness of the sensing lines 618, 718, 818 are 10 and 5 μm, those of the heating lines 616, 716, 816 are preferably about 20 μm and 5 μm, respectively.

As illustrated above, the present invention provides advantages that the heater line is apart from the silicon substrate and the gas sensitive material of ceramic is formed in a bulky shape so that the heat capacity and the heat loss are minimized to obtain the gas sensor with low power consumption and low manufacturing cost. Therefore, the gas sensor of the present invention can be widely applied to the device such as a portable gas detection apparatus. Moreover, in comparison with the prior art gas sensor, there are another merit that only two masks are needed for patterning the window and the metal pattern in the method for manufacturing the gas sensor, and further, mass productivity of semiconductor manufacture process such as a batch process can be still applied to the present invention as it is so that the cost for the manufacture can be lowered.

While the present invention has been described with respect to certain preferred embodiments only, other modifications and variation may be made without departing from the spirit and scope of the present invention as set forth in the following claims.

What is claimed is:

1. A gas sensor, comprising:
    a silicon substrate provided with a recess formed by patterning to a predetermined depth;
    an insulating layer formed on top of the silicon substrate except at the recess;
    a heating line crossing the recess and being fixed to the insulating layer, to be electrically isolated from the silicon substrate, said heating line comprising at least one U-shaped bend;
    a sensing line crossing the recess and being fixed to the insulating layer, to be electrically isolated from the silicon substrate and the heating line, said sensing line comprising at least one branch inserted within one of said U-shaped bends; and
    a gas detecting portion formed on predetermined portions of the heating line and the sensing line.

2. The gas sensor as recited in claim 1, wherein the silicon substrate has a crystal orientation of <100>.

3. The gas sensor as recited in claim 1, wherein the heating line and the sensing line further comprise a pair of metal pads configured to be electrically connected to a circuit.

4. The gas sensor as recited in claim 3, wherein the heating line and the sensing line are made of material selected from a group consisting of platinum (Pt), nickel (Ni) doped with gold (Au) or palladium (Pd), and multicrystal silicon doped with boron.

5. The gas sensor as recited in claim 1, wherein the insulating layer is of material selected from a group consisting of silicon oxide, silicon nitride and silicon carbide.

6. A method for manufacturing a gas sensor, the method comprising:
    forming an insulating layer on a silicon substrate;
    forming a window by patterning a portion of the insulating layer;

forming a heating line and a sensing line upon the silicon substrate exposed by the window and the insulating layer, said heating line comprising at least one U-shaped bend and said sensing line comprising at least one branch inserted within one of said U-shaped bends;

separating the heating line and the sensing line from the silicon substrate by dipping the silicon substrate into alkaline aqueous solution to pattern the substrate exposed to the window and to form a recess with a shape of the window; and forming a gas detecting portion on predetermined portions of the heating line and the sensing line which are formed over the recess.

7. The method as recited in claim 6, wherein the silicon substrate has a crystal orientation of <100>.

8. The method as recited in claim 6, wherein the insulating layer is of material selected from the group consisting of silicon oxide, silicon nitride and silicon carbide.

9. The method as recited in claim 6, wherein the heating line and the sensing line are of material selected from a group consisting of platinum (Pt), nickel (Ni) doped with gold (Au) or palladium (Pd), and multi-crystal silicon doped with boron.

10. The method as recited in claim 6, wherein the heating line is electrically isolated from the sensing line.

11. The method as recited in claim 6, wherein the alkaline aqueous solution is potassium hydroxide or a mixture of ethylenediamine and pyrocatechol.

* * * * *